United States Patent [19]

Yamada

[11] 4,171,176
[45] Oct. 16, 1979

[54] FLEXIBLE BAR REINFORCED CONCRETE PILE AND METHOD OF CONSTRUCTION

[75] Inventor: Kunimitsu Yamada, Tokyo, Japan

[73] Assignees: Taisei Corporation; Neturen Co. Ltd., both of Tokyo, Japan

[21] Appl. No.: 827,811

[22] Filed: Aug. 25, 1977

[30] Foreign Application Priority Data

Sep. 28, 1976 [JP] Japan .................... 51-115401

[51] Int. Cl.² ............................................. E02D 5/18
[52] U.S. Cl. .................................... 405/257; 405/239
[58] Field of Search ............. 61/53.5, 53.62, 53.6, 61/53.52, 53, 56, 56.5

[56] References Cited

U.S. PATENT DOCUMENTS

| | | | |
|---|---|---|---|
| 1,068,779 | 7/1913 | Kenny | 61/53.62 X |
| 1,080,283 | 12/1913 | Kenny | 61/53.62 X |
| 1,087,334 | 2/1914 | Stevens | 61/53.62 X |
| 2,789,419 | 4/1957 | Pickman | 61/53.62 X |
| 3,060,694 | 10/1962 | Holmes | 61/53.62 |
| 4,027,491 | 6/1977 | Turzillo | 61/53.5 X |

*Primary Examiner*—Dennis L. Taylor
*Attorney, Agent, or Firm*—Wenderoth, Lind & Ponack

[57] ABSTRACT

A flexible bar reinforced concrete pile is provided herein composed of a steel tube containing therein a plurality of jointless high-strength flexible bars, strands or bundles of bar or strand located axially along the inside wall of said steel tube, the remaining space within the steel tube being packed with prepacked concrete or mortar, and a method for constructing the same.

12 Claims, 31 Drawing Figures

FLEXIBLE BAR REINFORCED CONCRETE PILE AND METHOD OF CONSTRUCTION

BACKGROUND OF THE INVENTION

The present invention relates to a flexible bar reinforced concrete pile and the method of its construction.

The flexible bar reinforced concrete pile according to the present invention represents a steel tube internally holding individual jointless high-strength flexible bars or a plurality of jointless high-strength flexible bars bundled together (hereinafter referred to as a high-strength flexible bar bundle) in the axial direction with the internal space of said steel tube being filled with prepacked concrete or mortar.

The flexible bar reinforced concrete pile can be constructed in the field as described below.

At first, a steel tube is dropped into a dug pit; individual jointless high-strength flexible bars or high-strength flexible bar bundles are then laid in the axial direction of the steel tube; these bars or bar bundles are anchored in a suspended state in a steel tube and then, prepacked concrete or mortar is placed into the tube.

DESCRIPTION OF THE PRIOR ART

It is well known that a reinforced concrete structure is an integral structure in which the concrete withstands the compression as the bar withstands the tension. Therefore, in a reinforced concrete structure, in order to increase the bending strength of the structure by way of increasing the tensile strength of the reinforcing bar, it is also necessary to increase the compressive strength of the concrete.

Figure 18A:
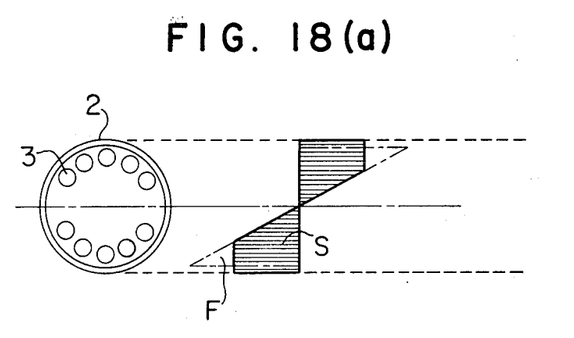
FIG. 18(a) is a plan view showing the allowable stress intensity in the flexible bar-reinforced concrete pile according to the present invention.
Figure 18B:
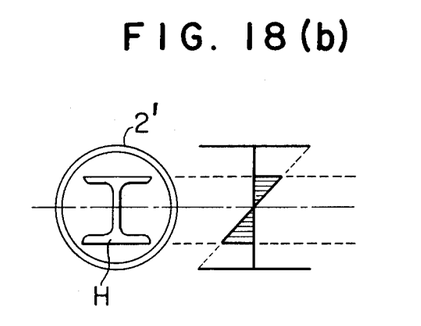
FIG. 18(b) is a plan view showing the allowable stress intensity in the conventional concrete pile with enclosed H-steel.

As illustrated in FIG. 18(b), an H-type steel is axially laid in a steel tube 2' and the internal space is filled with concrete producing a pile having an increased bend-compression strength. In such a pile, the intention is to reduce the strain normal to the pile section through cooperation between the tube, concrete and H-type steel, thereby preventing a compressive failure of the concrete. In such a pile, however, a slight increase in the resistance of the concrete to the compressive failure is recognized only in the axial center portion of the pile. No effect is observed in the portion close to the tube wall where increased strength is most required. Thus, in spite of the presence of an H-type steel, any appreciable increase in the strength in a direction normal to the pile section cannot be expected from such a pile.

In view of this situation, the demand has increased for a concrete pile having a relatively small diameter and a high bending resistance moment which permits easy construction in the field.

SUMMARY OF THE INVENTION

With the above discussion in mind, the first object of the present invention is to lay a required number of high-strength flexible bars or bar bundles in the axial direction of a steel tube and then to fill the internal space of said tube with prepacked concrete or mortar. The restraining effect of the tube increases the compressive strength of the prepacked mortar or concrete. Therefore, the interaction with the high-strength flexible bars, which share the tension load, drastically increases the bending resistance moment and the ultimate moment of the pile section.

The second object of the present invention is to lay, as close as possible to the tube wall, a plurality of high-strength flexible bars or bar bundles in the axial direction of the tube, thereby drastically increasing the moment of inertia of the area. This results in the ability of the pile to resist creep failure even when a high tension stress develops therein, because of the interaction between the external steel tube and the internal high-strength flexible bars or bar bundles.

The third object of the present invention is to provide a reinforced concrete pile with a uniformly high sectional strength over its entire length.

The fourth object of the present invention is to provide a concrete pile with a high ultimate resistance which can be executed efficiently by digging a pit of a relatively small sectional area and using a steel tube having a small diameter.

The present invention relates to a flexible bar-reinforced concrete pile and the method of its construction.

The flexible bar reinforced concrete pile according to the present invention represents a steel tube in which individual high-strength flexible bars or high-strength flexible bar bundles are laid in the axial direction and then the internal space is packed with prepacked concrete or mortar. It is desirable for workability that the flexible bar be one with a plurality of spiral grooves formed at a specified pitch on the surface, though it may also be a high-strength stranded bar.

Further, the tensile strength of the flexible bar is desirably set in the range of 90–200 $kg/mm^2$ against 30–60 $kg/mm^2$ of the steel tube, so that the steel tube will not suffer creep failure even when a heavy tension stress acts on the pile.

The flexible bar-reinforced concrete pile according to the present invention is constructed in the field by the following method. A pit is dug and a steel tube is placed therein. Next, individual jointless high-strength flexible bars or bar bundles are laid in the axial direction of the tube. Then, with each bar or each bar bundle anchored in a suspended state, the internal space of the tube is packed with prepacked concrete or mortar. If the pit is excavated by the mud-water method, it will be desirable to provide a bottom plate at the base of the steel tube and sink the tube with a counterweight attached thereto to overcome the bouyancy of the mud water.

DESCRIPTION OF THE DRAWINGS

Other objects, features and advantages of the present invention will become apparent from the following detailed description in conjunction with the attached drawings.

DESCRIPTION OF THE PREFERRED EMBODIMENTS

The present invention is to be described in detail referring to the embodiments illustrated in FIGS. 1 to 18(b).

Figure 1:
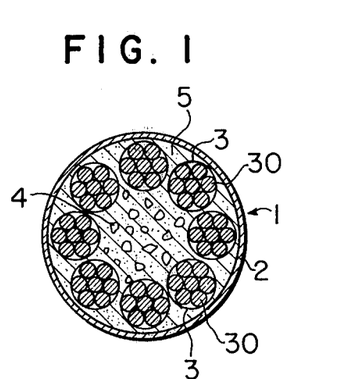
FIG. 1 is a plan view of the flexible bar reinforced concrete pile according to the present invention with the flexible bar bundle depicted being disproportionately larger than the other parts.
Figure 2:
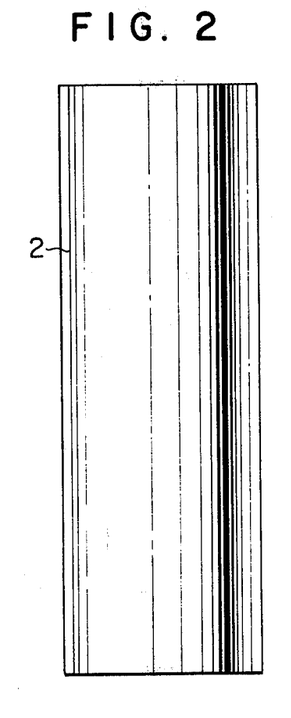
FIG. 2 is a front elevation view corresponding to FIG. 1.
Figure 3:
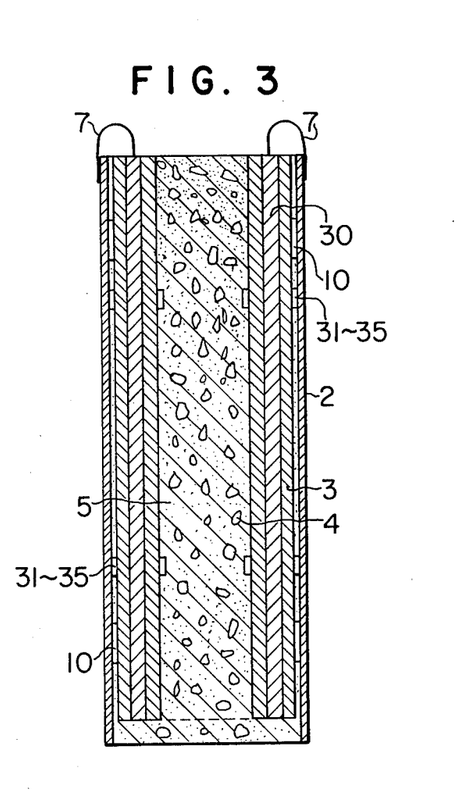
FIG. 3 is a longitudinal sectional view corresponding to FIG. 2.

FIGS. 1 to 3 show the structure of a flexible bar reinforced concrete pile. In these figures, 1 is the flexible bar reinforced concrete pile. Along the inside wall of the steel tube 2, a required number of jointless high-strength flexible bar bundles 3 are laid with a specified spacing. The flexible bar bundle 3 is composed of a plurality of individual flexible bars 30, bundled together by means of spacers 31–35 as illustrated in FIGS. 4(a) to 5(e).

The numbers of individual high-strength flexible bars and bar bundles to be laid along the inside wall of the steel tube depend on the required design strength of the pile.

Use of the spacers in bundling the individual bars is for the purpose of increasing the bond area of the bar and concrete by filling the space between the individual bars with mortar, thus enhancing the workability in bundling.

FIGS. 4(a)–FIG. 6 illustrate spacers used for these purposes.

Figure 4A:
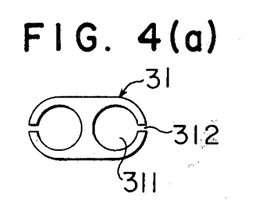
FIGS. 4(a)–(e) are plan views of spacers to be used for forming a bundle of individual flexible bars.
Figure 4B:
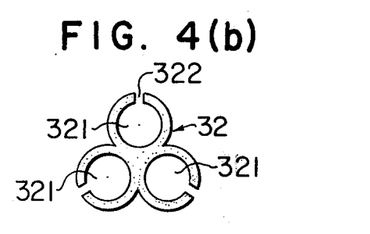
Figure 4C:
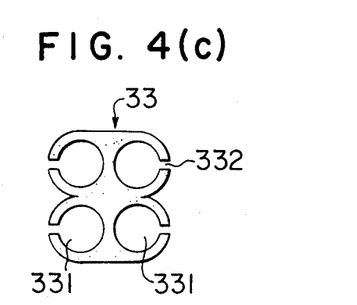
Figure 5A:
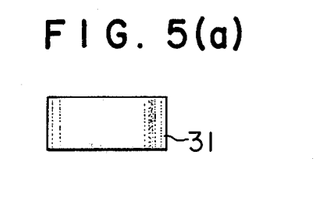
FIGS. 5(a), (b), (c), (d), and (e) are front elevation views corresponding to FIGS. 4(a), (b), (c), (d) and (e), respectively.
Figure 5B:
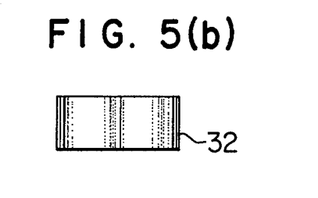
Figure 5C:
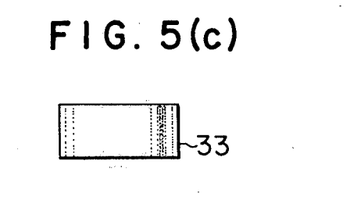

FIGS. 4(a) and 5(a) show two holes 311 which receive the individual flexible bars 30 being provided, thereby forming a nearly rectangular pattern 31. FIGS. 4(b) and 5(b) show three similar holes 321 being provided, thereby forming a nearly triangular pattern 32. FIGS. 4(c) and 5(c) show four holes 331 being provided, thereby forming a pattern 33.

Figure 4D:
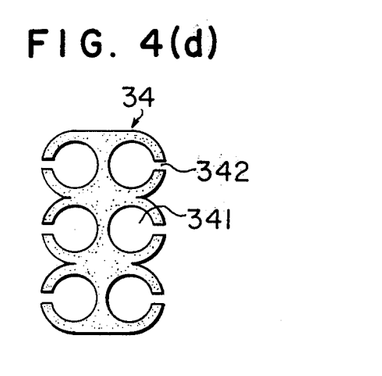
Figure 4E:
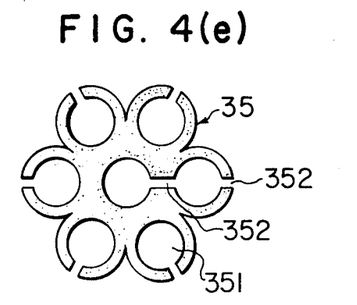
Figure 5D:
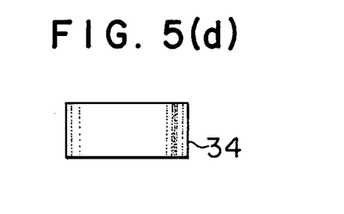
Figure 5E:
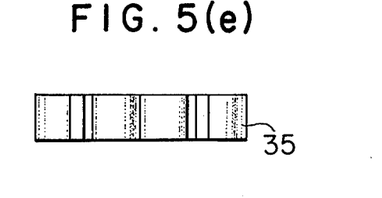

FIGS. 4(d) and 5(d) show six holes 341 being provided, thereby forming a pattern 34. FIGS. 4(e) and 5(e) illustrate seven holes 351 being provided, thereby forming a pattern 35.

The spacer is made of an elastic, flexible synthetic resin.

In FIGS. 4(a)–5(e), 312, 322, 332, 342 and 352 are the openings to receive the individual flexible bars.

To make a bundle of individual high-strength flexible bars 30 by means of the above-mentioned spacers, a plurality of individual high-strength flexible bars coiled within the elastic limit are uncoiled and laid out parallel to one another.

Then, one bar after another is pressed through each hole.

Figure 6:
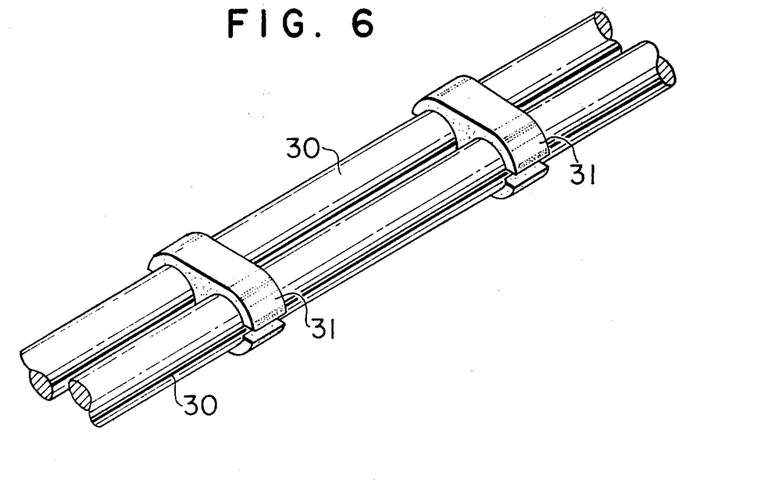
FIG. 6 is an oblique view showing two individual high-strength flexible bars bundled together using a spacer illustrated in FIG. 4(a).
Figure 17:
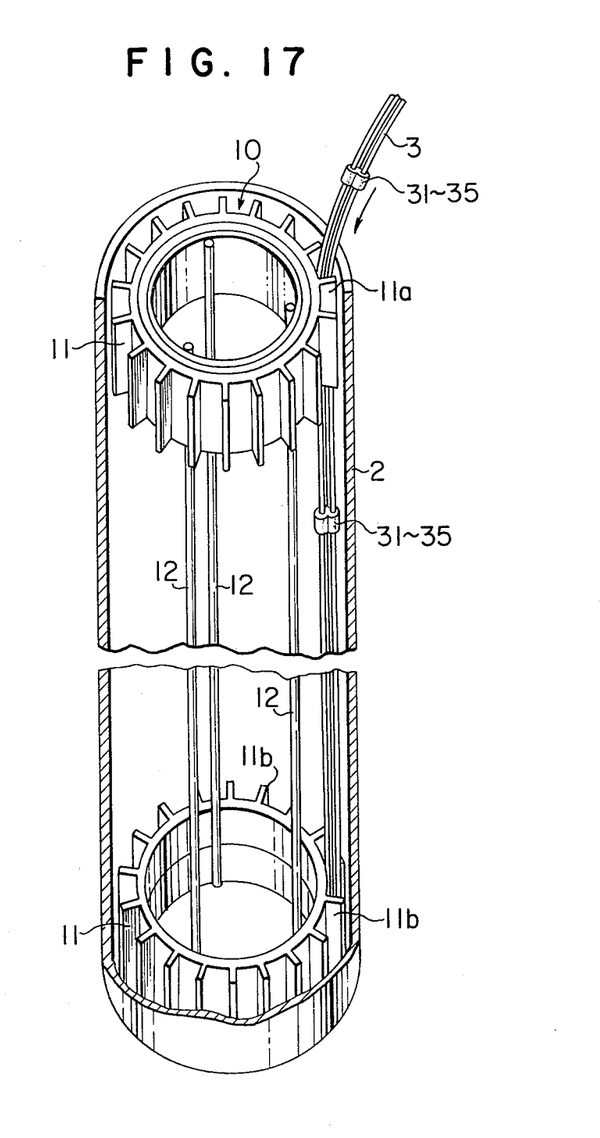
FIG. 17 is an oblique view of an example of the spacer to be used in laying flexible bar bundles in the axial direction of the steel tube according to the method of the present invention.

The spacers being elastic and flexible, the opening is deformed and enlarged by the pressing force when the bar 30 is inserted, thereby facilitating such insertion. After the individual bar has been inserted into the hole, which has a preset diameter about equal to or somewhat larger than the outer diameter of said bar, said opening is restored to its original width. Thus, using the spacer as shown in FIGS. 4(a) and 5(a), two individual flexible bars 30 as shown in FIG. 6 can be bundled together with a specific spacing by means of the spacer 31. By providing such spacers at adequate intervals and successively inserting the individual flexible bars 30 into a required number of holes, a high-strength flexible bar bundle 3 is formed and then cut to a required length. The high-strength flexible bar bundle 3 thus formed is laid close to the inside wall of the steel tube 2 using the spacer 10 as illustrated for instance in FIG. 17. The spacer 10 is constituted by linking a hollow body 11 with axial fins 11a formed at a specific pitch on the outside to a hollow body 11' with similar axial fins 11b by means of a connection piece 12. The fins on the hollow body 11' are designed to fall on the same vertical line as the fins on the corresponding hollow body 11. Depending on the length of the pile, in addition to two hollow bodies 11, upper and lower, there are provided an adequate number of intermediate ones. The spacers 10 thus constituted are placed immovably in the steel tube 2. The high-strength flexible bar bundles 3 thus formed are laid axially within the steel tube between the fins 11a and the corresponding fins 11b of the spacers 10. Thereupon, using the hooks provided at the top edge of the steel tube 2, said bundles 3 are anchored in a suspended state along the inside wall of the steel tube 2. After several repetitions of this process, a plurality of high-strength flexible bar bundles can be disposed along the inside wall of the steel tube 2. The above example refers to the case wherein the spacers 10 are placed within the steel tube 2, and then the high-strength flexible bars 30 or bar bundles 3 are laid between the fins 11a and 11b of the spacers 10. As the occassion requires, however, before insertion into the steel tube 2, said flexible bars or bar bundles may be laid successively between the fins 11a and 11b of said spacers 10. After binding the spacers 10 with iron wires so that said bars or bar bundles may dislocate outside the fins 11a and 11b, said bars or bar bundles may be inserted into the steel tube 2, and then, the internal space of said tube may be packed with prepacked concrete or mortar.

Figure 7A:
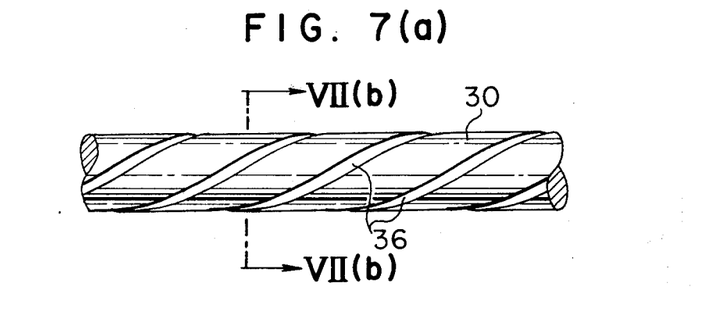
FIG. 7(a) is an enlarged front view of a preferred embodiment of the individual flexible bar according to the present invention.
Figure 7B:
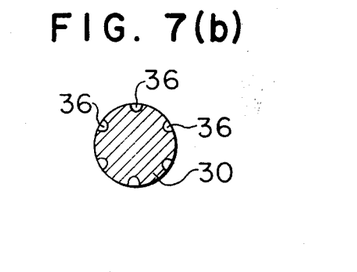
FIG. 7(b) is a sectional view along the line 7b—7b of FIG. 7(a).

Thus, the space in the steel tube holding a group of flexible bar bundles 3 is packed with prepacked concrete 4 or mortar. When the space in the steel tube is packed with prepacked concrete, the flexible bar bundle 3 is made immovable by the mortar 5 in the state of being forcibly pressed against the corresponding wall of the steel tube through at least the thickness of the solid part of the spacer by means of the prepacked concrete aggregate. More desirable results will be obtained if a high-strength stranded bar with better bonding to the mortar is employed than if a bar with a circular section is employed. If a bar, as illustrated in FIGS. 7(a) and (b), with a plurality of spiral grooves 36 formed at a specific pitch on the outside is employed, because the mortar 5 filling said grooves 36 enhances the bonding, the bar can be integrated with the steel tube. Meanwhile, the bar illustrated in FIGS. 7(a) and (b) has an identical sectional area over the entire length and has no joint. Therefore, there is no possibility of unstranding as in the case of a stranded bar. Thus, it has the advantage of being able to maintain the same strength over the entire length. If a steel bar with a plurality of helical grooves 36 formed at a specific pitch on the surface is made of a material with, e.g. $C \leq 0.29\%$, $Mn \leq 1.80\%$, $P \leq 0.050\%$ and $S \leq 0.050\%$; has spiral grooves as shown in FIGS. 7(a) and (b) formed by the drawing die; is heated to, e.g. 950° C., quenched, and then tempered at 400° C., said bar will have a tensile strength of 150 kg/mm$^2$, a yield stress of 140 kg/mm$^2$ and an elongation of 8%. It will provide an appropriate high-strength flexible bar to make a high-strength concrete pile as will be described in detail later. If the strength of the flexible bar is set at about 90-200 kg/mm$^2$, which is higher than 30-60 kg/mm$^2$ set for the steel tube, the total sectional area of the bars to be laid in a pile is designed to be equal to the sectional area of the steel tube. And, if the number of bars required to meet this design are provided in the pile, the steel tube will be able to stand a bend-tension stress theoretically exceeding the elastic limit of the steel tube, within the plastic limit without suffering a creep failure.

Referring to FIGS. 10-17, the method of constructing in the field the flexible bar-reinforced concrete pile according to the present invention will be described.

Figure 10:
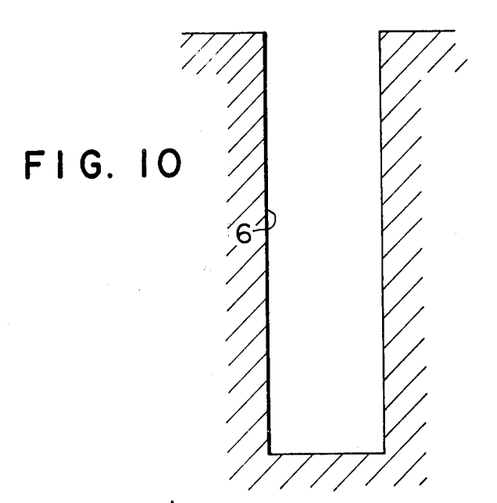
FIGS. 10 to 15 are respectively longitudinal sectional views illustrating the method of constructing in the field the flexible bar-reinforced concrete pile according to the present invention.
Figure 11A:
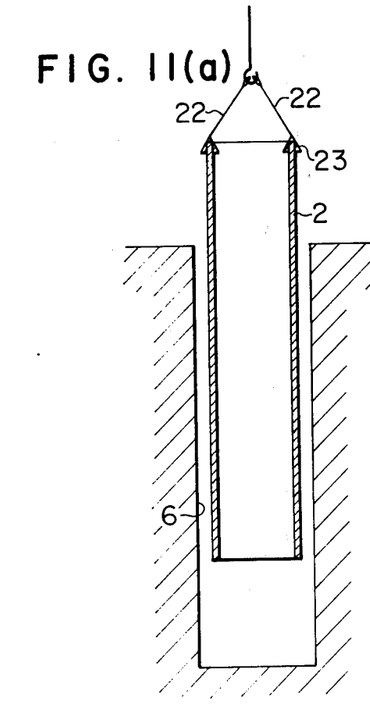
Figure 12A:
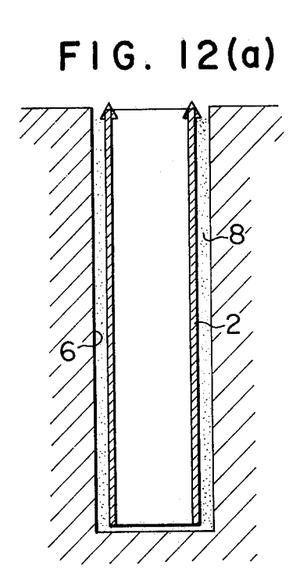
Figure 14:
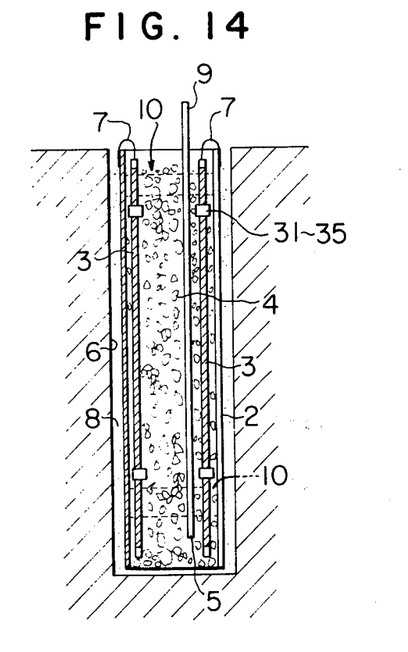
Figure 15:
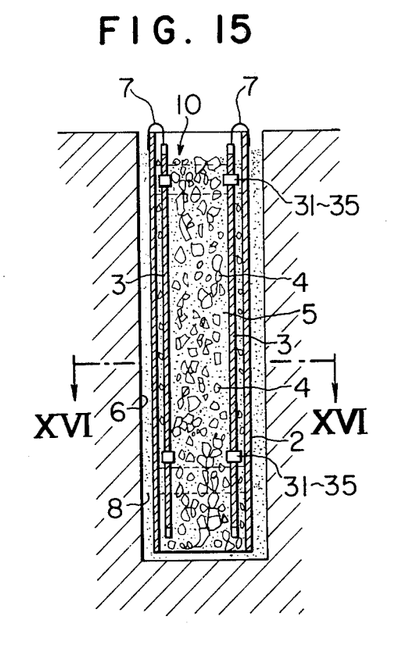
Figure 16:
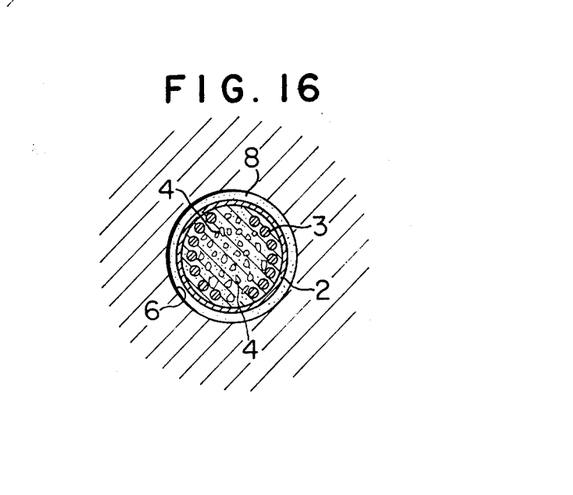
FIG. 16 is a sectional view along XV—XV of FIG. 15.

First, a pit 6 as shown in FIG. 10 is dug at the intended site of driving the flexible bar-reinforced concrete pile according to the present invention. A steel tube 2 of a specified diameter is placed as shown in FIG. 11(a) in the pit 6, 22 being a suspension wire with one end fixed to the top edge 23 of the steel tube. After the steel tube 2 settles to the bottom of the pit 6, as illustrated in FIG. 12(a), the space between the outer wall of the steel tube 2 and the pit 6 is packed with mortar or other hardening agent 8. Thereupon, the spacer 10 described above referring to FIG. 17 is laid within the tube. Then, the flexible bar bundles 3 each composed of a specific number of individual flexible bars 30 bundled together using the spacer described referring to FIGS. 4(a)-6 are successively inserted between the fins of the spacer 10. With a gap retained between the base of the bar and the bottom of the pit, said bundles are anchored in a suspended state using the hooks 7 provided at the top edge of the steel tube 2. After repetitions of this process, groups of flexible bars 3 are arranged at specific intervals around the inside wall of the steel tube 2. Next, as illustrated in FIG. 14, the space in the steel tube 2 is packed with prepacked concrete aggregate when used with prepacked concrete. In this way, each flexible bar group is forcibly pressed against the inside wall of the steel tube 2 and the flexible bar bundle 3 adjoins the inside wall of the tube through the corresponding solid part of the spacer 10. Thereafter, the prepacked concrete mortar 5 is poured through a mortar charge pipe 9 which has been laid inside of each flexible bar group prior to packing with the prepacked concrete. Thus, the driving of the flexible bar-reinforced concrete pile according to the present invention is finished. The above example refers to the case wherein the pit 6 is manually dug.

Figure 11B:
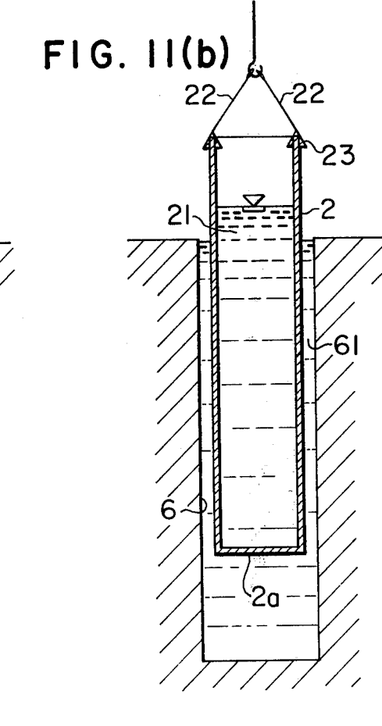
Figure 12B:
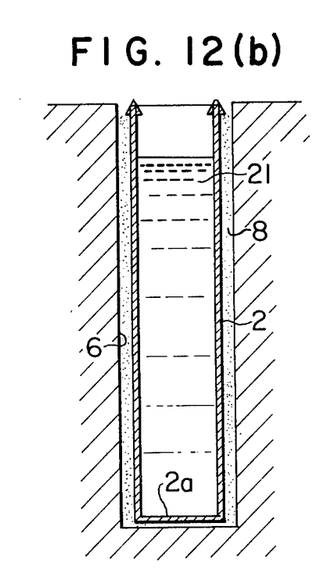
Figure 13:
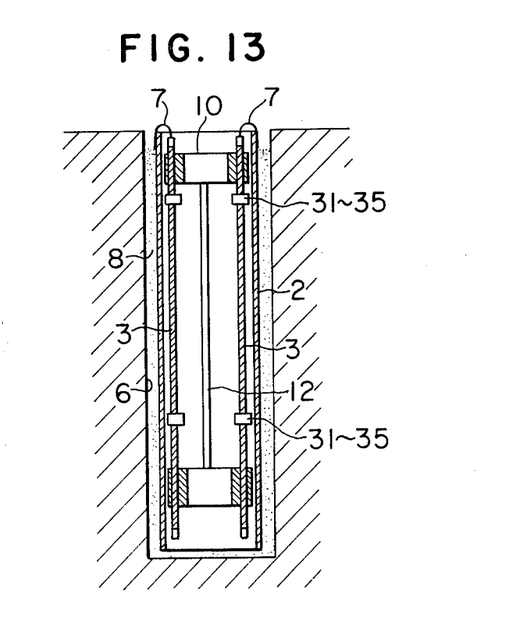

If a mud-water excavation method is employed, the steel tube has to be sunk in the pit filled with mud water 61. In the latter case, the steel tube 2 is provided with a bottom cap 2a as illustrated in FIG. 11(b). It is attached with a counterweight to the mud water 61 of the pit 6, i.e. a required volume of liquid 21 such as fresh water being held at the bottom of the tube, which enables the tube 2 to sink easily against the buoyancy of the mud water 61, as illustrated in FIG. 12(b). The subsequent process of positioning the steel tube 2 in the pit 6 is the same as described in the above example. It can be seen that the flexible bar bundle is anchored in a suspended state with no contact of its bottom with the base cap 2a of the tube 2.

Figure 8A:
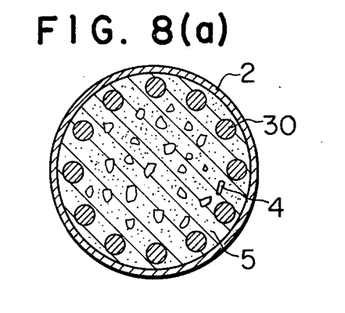
FIG. 8(a) is a plan view showing another embodiment of the present invention.
Figure 8B:
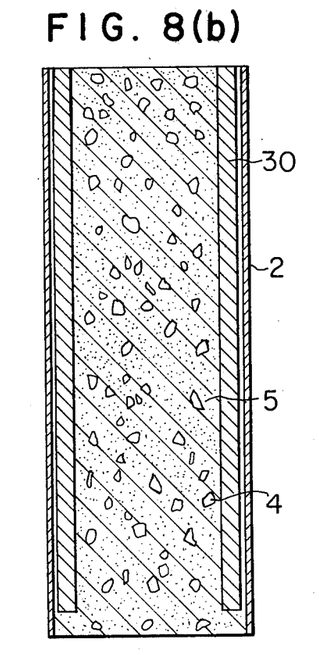
FIG. 8(b) is a longitudinal sectional view corresponding to FIG. 8(a).
Figure 9A:
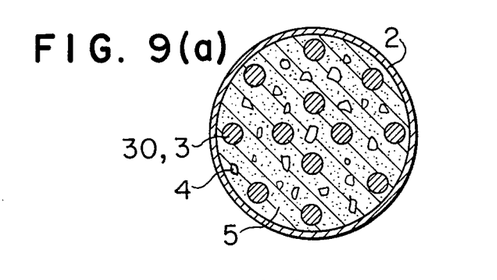
FIG. 9(a) is a plan view of still another embodiment of the present invention.
Figure 9B:
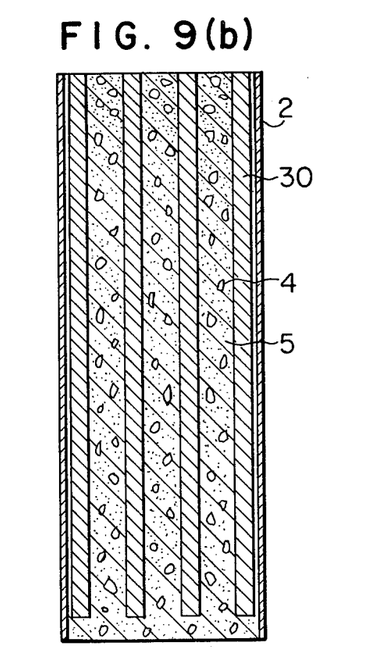
FIG. 9(b) is a longitudinal sectional view corresponding to FIG. 9(a).
Figure 9C:
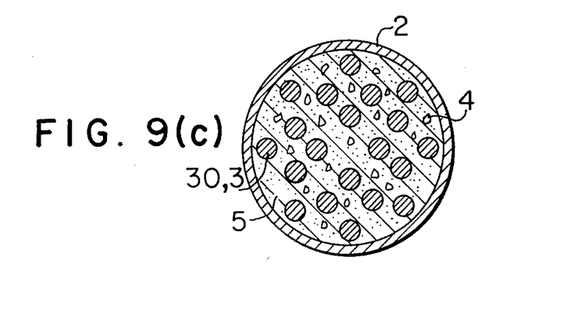
FIG. 9(c) is a plan view of the third embodiment of the present invention.

The above example refers to a case of a required number of high-strength flexible bar bundles 3 being axially arranged within the steel tube. However, when the steel tube is relatively small in diameter, a required number of individual high-strength flexible bars 30 may, as illustrated in FIGS. 8(a) and (b), be laid along the inside of the tube 2. In the latter case, the spacers 31-35 shown in FIGS. 4(a)-5(e) are unnecessary. More desirable results with an increased resisting moment of the entire section and over the entire length of the pile would be obtained if, as illustrated in FIGS. 9(a), (b) and (c), a necessary number of high-strength flexible bars 30 or bar bundles 3 were laid along the central axis as well as along the inside wall of the tube or arranged at specific intervals in the intermediate space. Meanwhile, the mixed ratio between aggregate and mortar with which to fill the space in the tube is no different than the conventional value in the known prepacked concreting method, i.e. 20-25%.

The features of the present invention are more specifically set forth below.

(1) Since the steel tube is constituted with jointless, perfectly continuous, high-strength flexible bars successively anchored as reinforcing elements therein, the steel tube can be constructed with a shortened work period.

(2) The restraining effect of the steel tube increases the compressive strength of prepacked mortar, while interaction with the tension load-sharing and high-strength flexible bar group remarkably increases the bend resisting moment of the pile.

(3) Since the prepacked concrete mortar covers the steel tube 2, the individual flexible bars mainly bearing the tension are favorably protected from exposure to the atmosphere even when a tensile crack develops in the concrete of the pile in service. Accordingly, the bars remain free from corrosion. Thus, with no allowance being necessary for corrosion of the individual flexible bars due to tensile cracks, the gap between the inside wall of the steel tube and the flexible bar group can be minimized so far as the bonding stress to be transmitted through the bar group is concerned. Accordingly, with the flexible bar groups around the wall of the steel tube, the moment of inertia of area can be drastically increased. As illustrated in FIG. 18, the conventional H-steel enclosing concrete pile has merely an allowable stress intensity as indicated by an oblique line at the right in FIG. 18(b). The concrete pile of the present invention has a remarkably increased area of inertia as indicated in FIG. 18(a). In FIG. 18(a), S denotes the allowable stress intensity of the steel tube and F denotes that of the flexible bar of bar bundle.

(4) The bend-tension stress acting on the pile is shared between the steel tube and the flexible bar group. Meanwhile, because the strength of an individual flexible bar is extremely high, an extremely high allowable stress intensity is obtained. Even when a bend-tension stress working outside surface of the steel tube exceeds the elastic limit of said tube, the internal flexible bar group still remains within the elastic limit. Therefore, the steel tube can resist the stress within the plastic limit without suffering a creep failure. Thus, as compared with a case of a steel tube being coupled with an ordinary bar group of not particularly high strength, i.e. equally strong members being coupled, the pile according to the present invention is characterized by excellent toughness and sectional strength.

(5) With disposition of high-strength flexible bars or bar bundles along the central axis and in the intermediate space as well as along the inside wall of the steel tube, the resistance of the pile to the shear stress on all sections and over the entire length of the pile can be drastically increased.

(6) Unlike the conventional method which makes it necessary to dig a pit of a large diameter and using a concrete pile of a large diameter when the pile is required to be stronger, the invented method enables formation of a high-strength pile on a substantially smaller work scale.

What is claimed is:

1. A flexible bar reinforced concrete pile comprising a steel tube containing therein a plurality of jointless high-strength flexible bars, strands or bundles of bars or strands located axially along the inside wall of said steel tube, and the remaining space within the steel tube being packed with prepacked concrete or mortar, said concrete pile being such that the high-strength flexible bars, strands or bundles of bar or strand are not anchored to the steel tube at the ends thereof and being further characterized in that said bars, strands or bundles of bars or strands do not extend to the entire length of the tube so that at least one end of said steel tube extends beyond the length of said high-strength flexible bars, strands or bundles of bars or strands and wherein the steel tube has a tensile strength of 30–60 kg/mm$^2$ and each individual high strength flexible bar and strand have a tensile strength of 90–200 kg/mm$^2$.

2. A flexible bar reinforced concrete pile of claim 1, wherein flexible bars, strands or bundles of bar or strand are additionally laid along the central axis of the steel tube and in the longitudinal direction with a specific spacing therebetween.

3. A flexible bar reinforced concrete pile according to claim 1, wherein high-strength flexible bars, strands or bundles of bar or strand are additionally laid along the central axis as well as in the intermediate space between the central axis and inside wall of the steel tube with a specific spacing between said bar or strand.

4. A flexible bar reinforced concrete pile according to claim 1, wherein said steel tube has a tensile strength of 30–60 kg/mm$^2$ and each individual high strength flexible bar and strand have a tensile strength of 90–200 kg/mm$^2$.

5. A flexible bar reinforced concrete pile according to claim 1, wherein the steel tube is capped at the end, which extends beyond said flexible bars, strands or bundle or bar or strand, with a steel plate.

6. A flexible bar reinforced concrete pile according to claim 1, wherein said individual flexible bars have a plurality of spiral grooves provided on the surface at a specific pitch.

7. The method of constructing a flexible bar reinforced concrete pile which comprises placing a steel tube into a dug pit designed to receive said steel tube, inserting a plurality of jointless high-strength flexible bars, strands or bundles of bars or strands along the inside wall of said steel tube in such a manner that the lower end of said flexible bars or strands do not touch the bottom plate of said steel tube, said bars or strands being suspended so that they extend along the inside of the tube in the longitudinal direction by anchoring means, and then packing the remaining space in said steel tube with prepacked concrete or mortar, wherein said steel tube has a tensile strength of 30–60 kg/mm$^2$ and each individual high strength flexible bar and strand have a tensile strength of 90–200 kg/mm$^2$.

8. A method according to claim 7, wherein prior to laying said flexible bars, strands or bundles of bar or strand in said steel tube, spacers with fins on the outside surface thereof are placed in said steel tube so that said bars or strands can be inserted along the fins provided on the outside surface of said spacers.

9. A method according to claim 7, wherein flexible bars, strands or bundles of bar or strand are additionally laid along the central axis of the steel tube with a specific spacing therebetween.

10. The method according to claim 7, wherein flexible bars, strands or bundles of bar or strand are additionally laid along the central axis and also in the intermediate space between the central axis and inside wall of said steel tube with a spacific spacing therebetween.

11. The method according to claim 7, wherein said flexible bars, strands or bundles of bar or strand are assembled with a spacer and these assemblies are then inserted in the steel tube.

12. The method according to claim 7, wherein the pit is dug by the mud water excavation method and said steel tube capped at the base and attached with a counter weight to overcome the bouyancy of the mud water is sunk in the pit.

* * * * *